(12) United States Patent
Casey

(10) Patent No.: US 9,320,627 B2
(45) Date of Patent: Apr. 26, 2016

(54) FLEXIBLE STENT WITH TORQUE-ABSORBING CONNECTORS

(75) Inventor: Brendan J. Casey, Galway (IE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

(21) Appl. No.: 13/411,135

(22) Filed: Mar. 2, 2012

(65) Prior Publication Data

US 2012/0165921 A1 Jun. 28, 2012

Related U.S. Application Data

(63) Continuation of application No. 11/973,707, filed on Oct. 9, 2007, now Pat. No. 8,128,679, which is a continuation-in-part of application No. 11/805,584, filed on May 23, 2007, now Pat. No. 8,016,874.

(51) Int. Cl.
*A61F 2/915* (2013.01)

(52) U.S. Cl.
CPC ....... *A61F 2/915* (2013.01); *A61F 2002/91541* (2013.01); *A61F 2002/91558* (2013.01); *A61F 2250/0031* (2013.01)

(58) Field of Classification Search
CPC .................................................. A61F 2/885
USPC ...................... 623/1.15, 1.16, 1.22
See application file for complete search history.

(56) References Cited

U.S. PATENT DOCUMENTS

| | | | |
|---|---|---|---|
| 4,475,972 A | 10/1984 | Wong | |
| 4,580,568 A | 4/1986 | Gianturco | |
| 4,738,740 A | 4/1988 | Pinchuk et al. | |
| 4,743,252 A | 5/1988 | Martin, Jr. et al. | |
| 4,759,757 A | 7/1988 | Pinchuk | |
| 4,776,337 A | 10/1988 | Palmaz | |
| 4,800,882 A | 1/1989 | Gianturco | |
| 4,907,336 A | 3/1990 | Gianturco | |
| 5,015,253 A | 5/1991 | MacGregor | |
| 5,019,090 A | 5/1991 | Pinchuk | |
| 5,041,126 A | 8/1991 | Gianturco | |
| 5,053,048 A | 10/1991 | Pinchuk | |

(Continued)

FOREIGN PATENT DOCUMENTS

| | | |
|---|---|---|
| CA | 2309079 | 11/2004 |
| EP | 0357003 | 3/1990 |

(Continued)

OTHER PUBLICATIONS

U.S. Appl. No. 60/637,495, filed Dec. 20, 2004, Fierens et al.

(Continued)

*Primary Examiner* — Yashita Sharma
*Assistant Examiner* — Seema Mathew
(74) *Attorney, Agent, or Firm* — Workman Nydegger

(57) ABSTRACT

A stent includes an essentially tubular body formed by a web structure that is composed of a plurality of longitudinally adjacent web rings, each including a plurality of web elements that are disposed circumferentially around the longitudinal axis of the stent and that are adjoined one to the other by a junction bend. Each junction bend in a first web ring is coupled to another junction bend in a neighboring ring by a connector having a step-wise configuration, in which a central segment of the connector is disposed essentially parallel to the longitudinal axis of the stent and may become twisted to absorb torque imposed on the stent.

21 Claims, 8 Drawing Sheets

(56) References Cited

U.S. PATENT DOCUMENTS

| | | |
|---|---|---|
| 5,059,211 A | 10/1991 | Stack et al. |
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |
| 5,133,732 A | 7/1992 | Wiktor |
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,449,382 A | 9/1995 | Dayton |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenberg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A | 4/1998 | Danforth et al. |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,782,904 A | 7/1998 | White et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A * | 3/1999 | Starck .............. A61F 2/91 623/23.7 |
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,016 A * | 9/1999 | Jang .............. A61F 2/91 623/1.11 |
| 5,948,018 A | 9/1999 | Dereume et al. |
| 5,954,743 A | 9/1999 | Jang |
| 5,968,091 A | 10/1999 | Pinchuk et al. |
| 5,968,561 A | 10/1999 | Batchelder et al. |
| 5,980,552 A | 11/1999 | Pinchasik et al. |
| 5,984,965 A | 11/1999 | Knapp et al. |
| 6,017,365 A | 1/2000 | Von Oepen |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A * | 3/2000 | Jang .............. 623/1.15 |
| 6,042,597 A | 3/2000 | Kveen et al. |
| 6,048,361 A | 4/2000 | Von Oepen |
| 6,056,767 A | 5/2000 | Boussignac et al. |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A | 9/2000 | Szycher et al. |
| 6,123,721 A | 9/2000 | Jang |
| 6,132,460 A | 10/2000 | Thompson |
| 6,136,023 A | 10/2000 | Boyle |
| 6,152,957 A | 11/2000 | Jang |
| 6,165,212 A | 12/2000 | Dereume et al. |
| 6,168,409 B1 | 1/2001 | Fare |
| 6,174,326 B1 | 1/2001 | Kitaoka et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,210,429 B1 | 4/2001 | Vardi et al. |
| 6,231,598 B1 | 5/2001 | Berry et al. |
| 6,231,600 B1 | 5/2001 | Zhong |
| 6,241,762 B1 | 6/2001 | Shanley |
| 6,245,101 B1 | 6/2001 | Drasler et al. |

(56) References Cited

U.S. PATENT DOCUMENTS

| | | |
|---|---|---|
| 6,253,443 B1 | 7/2001 | Johnson |
| 6,258,115 B1 | 7/2001 | Dubrul |
| 6,258,116 B1 | 7/2001 | Hojeibane |
| 6,261,318 B1 | 7/2001 | Lee et al. |
| 6,261,319 B1 | 7/2001 | Kveen et al. |
| 6,264,688 B1 | 7/2001 | Herklotz et al. |
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 | 12/2001 | Wolinsky et al. |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,416,539 B1 | 7/2002 | Hassdenteufel |
| 6,436,132 B1 | 8/2002 | Patel et al. |
| 6,443,982 B1 | 9/2002 | Israel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 * | 1/2003 | Duerig et al. ............... 623/1.24 |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,562,065 B1 | 5/2003 | Shanley |
| 6,572,646 B1 | 6/2003 | Boylan et al. |
| 6,589,276 B2 | 7/2003 | Pinchasik et al. |
| 6,602,281 B1 | 8/2003 | Klein |
| 6,602,285 B1 | 8/2003 | Von Oepen et al. |
| 6,607,554 B2 | 8/2003 | Dang et al. |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,652,574 B1 | 11/2003 | Jayaraman |
| 6,676,701 B2 | 1/2004 | Rourke et al. |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,116 B1 | 5/2004 | Wolinsky et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Seibold et al. |
| 6,761,733 B2 | 7/2004 | Chobotov et al. |
| 6,770,088 B1 | 8/2004 | Jang |
| 6,776,793 B2 | 8/2004 | Brown et al. |
| 6,776,794 B1 | 8/2004 | Hong et al. |
| 6,786,922 B2 | 9/2004 | Schaeffer |
| 6,790,226 B2 * | 9/2004 | Edwin ............... A61F 2/86 623/1.13 |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 * | 4/2005 | Pinchasik et al. ............. 623/1.16 |
| 6,881,222 B2 | 4/2005 | White et al. |
| 6,896,697 B1 | 5/2005 | Yip et al. |
| 6,913,619 B2 | 7/2005 | Brown et al. |
| 6,916,336 B2 | 7/2005 | Patel et al. |
| 6,929,660 B1 | 8/2005 | Ainsworth et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,088 B1 | 6/2006 | Fischell et al. |
| 7,060,093 B2 | 6/2006 | Dang et al. |
| 7,070,614 B1 | 7/2006 | Neuss et al. |
| 7,128,756 B2 | 10/2006 | Lowe et al. |
| 7,141,062 B1 | 11/2006 | Pinchasik et al. |
| 7,179,286 B2 | 2/2007 | Lenz |
| 7,204,848 B1 | 4/2007 | Brown et al. |
| 7,329,277 B2 | 2/2008 | Addonizio et al. |
| 7,520,892 B1 | 4/2009 | Ainsworth et al. |
| 7,611,531 B2 | 11/2009 | Calisse |
| 7,625,398 B2 | 12/2009 | Clifford et al. |
| 7,686,843 B2 | 3/2010 | Moore |
| 7,766,956 B2 | 8/2010 | Jang |
| 7,789,904 B2 | 9/2010 | Von Oepen et al. |
| 7,789,905 B2 | 9/2010 | Oepen et al. |
| 7,794,491 B2 | 9/2010 | Oepen et al. |
| 7,811,314 B2 | 10/2010 | Fierens et al. |
| 7,815,672 B2 | 10/2010 | Von Oepen et al. |
| 7,815,763 B2 | 10/2010 | Fierens et al. |
| 7,842,078 B2 | 11/2010 | Von Oepen et al. |
| 7,842,079 B2 | 11/2010 | Von Oepen et al. |
| 7,846,196 B2 | 12/2010 | Von Oepen et al. |
| 7,850,726 B2 | 12/2010 | Casey |
| 7,867,272 B2 * | 1/2011 | Niermann ............... A61F 2/91 623/1.15 |
| 7,887,577 B2 | 2/2011 | Von Oepen et al. |
| 7,887,578 B2 | 2/2011 | Schneider |
| 7,927,364 B2 | 4/2011 | Fierens et al. |
| 7,927,365 B2 | 4/2011 | Fierens et al. |
| 8,016,874 B2 | 9/2011 | Casey |
| 8,034,097 B2 | 10/2011 | Neuss et al. |
| 8,088,157 B2 | 1/2012 | Fierens et al. |
| 8,128,679 B2 | 3/2012 | Casey |
| 2001/0007955 A1 | 7/2001 | Drasler et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0042647 A1 | 4/2002 | Jang |
| 2002/0055770 A1 | 5/2002 | Doran et al. |
| 2002/0058990 A1 * | 5/2002 | Jang ............... A61F 2/91 623/1.15 |
| 2002/0065549 A1 | 5/2002 | White et al. |
| 2002/0107560 A1 | 8/2002 | Richter |
| 2002/0111669 A1 | 8/2002 | Pazienza et al. |
| 2002/0113331 A1 | 8/2002 | Zhang et al. |
| 2002/0151964 A1 | 10/2002 | Smith et al. |
| 2002/0169499 A1 | 11/2002 | Zilla et al. |
| 2003/0055487 A1 | 3/2003 | Calisse |
| 2003/0083736 A1 * | 5/2003 | Brown ............... A61F 2/91 623/1.16 |
| 2003/0114918 A1 | 6/2003 | Garrison et al. |
| 2003/0120334 A1 | 6/2003 | Gerberding |
| 2004/0002753 A1 | 1/2004 | Burgermeister et al. |
| 2004/0024445 A1 * | 2/2004 | Dickson ............... A61F 2/91 623/1.19 |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0133271 A1 | 7/2004 | Jang |
| 2004/0167615 A1 * | 8/2004 | Lenz ............... A61F 2/91 623/1.16 |
| 2004/0230293 A1 | 11/2004 | Yip et al. |
| 2004/0243220 A1 | 12/2004 | Gianotti et al. |
| 2004/0267353 A1 | 12/2004 | Gregorich |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0184232 A1 | 8/2006 | Gianotti et al. |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0299505 A1 * | 12/2007 | Gregorich et al. ............. 623/1.15 |
| 2008/0077231 A1 | 3/2008 | Heringes et al. |
| 2008/0221664 A1 * | 9/2008 | Bales et al. ................. 623/1.22 |
| 2008/0294240 A1 * | 11/2008 | Casey ............... A61F 2/915 623/1.16 |
| 2009/0163992 A1 * | 6/2009 | Osman ............... A61F 2/91 623/1.15 |
| 2009/0163996 A1 * | 6/2009 | Bregulla ............... A61F 2/91 623/1.16 |

(56) References Cited

U.S. PATENT DOCUMENTS

| | | | |
|---|---|---|---|
| 2009/0163998 A1 | 6/2009 | Casey | |
| 2009/0264986 A1* | 10/2009 | Bales | A61F 2/88 623/1.22 |
| 2010/0057190 A1* | 3/2010 | Issenmann | A61F 2/856 623/1.16 |
| 2010/0114297 A1 | 5/2010 | Calisse | |
| 2010/0249903 A1* | 9/2010 | Wack | A61F 2/915 623/1.16 |
| 2011/0004289 A1 | 1/2011 | Oepen et al. | |
| 2011/0022159 A1 | 1/2011 | Fierens et al. | |
| 2011/0125243 A1 | 5/2011 | Schneider | |
| 2011/0144738 A1 | 6/2011 | Casey | |
| 2011/0270381 A1 | 11/2011 | Fierens et al. | |
| 2012/0277844 A1* | 11/2012 | Wu | A61F 2/915 623/1.11 |
| 2013/0218254 A1* | 8/2013 | Cattaneo | A61F 2/82 623/1.2 |
| 2013/0268055 A1* | 10/2013 | Cottone | A61F 2/915 623/1.16 |
| 2014/0277383 A1* | 9/2014 | Sachar | A61F 2/915 623/1.16 |

FOREIGN PATENT DOCUMENTS

| | | |
|---|---|---|
| EP | 0221570 | 1/1991 |
| EP | 565251 | 10/1993 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO 96/26689 | 2/1996 |
| WO | WO96/21404 | 7/1996 |
| WO | WO96/25124 | 8/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/39663 | 8/1999 |
| WO | WO99/49928 | 10/1999 |
| WO | WO00/13611 | 3/2000 |
| WO | WO00/18328 | 4/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/026164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 09/582,318, Aug. 14, 2002, Office Action.
U.S. Appl. No. 09/582,318, Mar. 7, 2003, Notice of Allowance.
U.S. Appl. No. 09/742,144, Sep. 24, 2002, Office Action.
U.S. Appl. No. 09/742,144, May 14, 2003, Office Action.
U.S. Appl. No. 09/742,144, Aug. 29, 2003, Notice of Allowance.
U.S. Appl. No. 09/916,394, Aug. 12, 2003, Office Action.
U.S. Appl. No. 09/916,394, Oct. 9, 2003, Office Action.
U.S. Appl. No. 09/916,394, Mar. 2, 2004, Office Action.
U.S. Appl. No. 09/967,789, Sep. 17, 2003, Office Action.
U.S. Appl. No. 09/967,789, Feb. 17, 2004, Notice of Allowance.
U.S. Appl. No. 10/241,523, Aug. 18, 2004, Office Action.
U.S. Appl. No. 10/241,523, Oct. 25, 2004, Office Action.
U.S. Appl. No. 10/241,523, Mar. 8, 2005, Office Action.
U.S. Appl. No. 10/241,523, Jun. 3, 2005, Office Action.
U.S. Appl. No. 10/241,523, Aug. 23, 2005, Office Action.
U.S. Appl. No. 10/241,523, Nov. 16, 2005, Office Action.
U.S. Appl. No. 10/241,523, Apr. 27, 2006, Office Action.
U.S. Appl. No. 10/743,857, Mar. 15, 2007, Office Action.
U.S. Appl. No. 10/743,857, Nov. 16, 2007, Office Action.
U.S. Appl. No. 10/743,857, May 8, 2008, Office Action.
U.S. Appl. No. 10/743,857, Jan. 6, 2009, Office Action.
U.S. Appl. No. 10/743,857, May 27, 2009, Office Action.
U.S. Appl. No. 10/743,857, Feb. 12, 2010, Notice of Allowance.
U.S. Appl. No. 10/743,857, Jun. 25, 2010, Notice of Allowance.
U.S. Appl. No. 10/743,857, Aug. 18, 2010, Issue Notification.
U.S. Appl. No. 10/859,636, Jun. 1, 2007, Office Action.
U.S. Appl. No. 10/859,636, Dec. 31, 2007, Office Action.
U.S. Appl. No. 10/859,636, Apr. 15, 2008, Office Action.
U.S. Appl. No. 10/859,636, Oct. 1, 2008, Notice of Allowance.
U.S. Appl. No. 10/859,636, Mar. 5, 2009, Office Action.
U.S. Appl. No. 10/859,636, Oct. 19, 2009, Notice of Allowance.
U.S. Appl. No. 10/859,636, Feb. 1, 2010, Notice of Allowance.
U.S. Appl. No. 10/859,636, May 19, 2010, Notice of Allowance.
U.S. Appl. No. 10/859,636, Dec. 9, 2010, Notice of Allowance.
U.S. Appl. No. 10/884,613, Mar. 30, 2005, Office Action.
U.S. Appl. No. 10/884,613, Nov. 14, 2005, Office Action.
U.S. Appl. No. 10/903,013, Mar. 15, 2007, Office Action.
U.S. Appl. No. 10/903,013, Nov. 19, 2007, Office Action.
U.S. Appl. No. 10/903,013, May 14, 2008, Office Action.
U.S. Appl. No. 10/903,013, Jan. 5, 2009, Office Action.
U.S. Appl. No. 10/903,013, May 27, 2009, Office Action.
U.S. Appl. No. 10/903,013, Feb. 12, 2010, Notice of Allowance.
U.S. Appl. No. 10/903,013, Jun. 24, 2010, Notice of Allowance.
U.S. Appl. No. 10/903,013, Aug. 18, 2010, Issue Notification.
U.S. Appl. No. 10/903,014, Mar. 15, 2007, Office Action.
U.S. Appl. No. 10/903,014, Nov. 16, 2007, Office Action.
U.S. Appl. No. 10/903,014, May 13, 2008, Office Action.
U.S. Appl. No. 10/903,014, Jan. 13, 2009, Office Action.
U.S. Appl. No. 10/903,014, Jun. 1, 2009, Office Action.
U.S. Appl. No. 10/903,014, Feb. 5, 2010, Notice of Allowance.
U.S. Appl. No. 10/903,014, May 26, 2010, Office Action.
U.S. Appl. No. 10/903,014, Jun. 24, 2010, Notice of Allowance.
U.S. Appl. No. 10/903,014, Aug. 25, 2010, Issue Notification.
U.S. Appl. No. 10/903,080, Mar. 15, 2007, Office Action.
U.S. Appl. No. 10/903,080, Nov. 19, 2007, Office Action.
U.S. Appl. No. 10/903,080, May 12, 2008, Office Action.
U.S. Appl. No. 10/903,080, Dec. 30, 2008, Office Action.
U.S. Appl. No. 10/903,080, May 27, 2009, Office Action.
U.S. Appl. No. 10/903,080, Jan. 13, 2010, Notice of Allowance.
U.S. Appl. No. 10/903,080, Sep. 16, 2010, Notice of Allowance.
U.S. Appl. No. 10/909,117, Aug. 22, 2007, Office Action.
U.S. Appl. No. 10/909,117, May 12, 2008, Office Action.

(56) References Cited

OTHER PUBLICATIONS

U.S. Appl. No. 10/909,117, Dec. 30, 2008, Office Action.
U.S. Appl. No. 10/909117, May 27, 2009, Office Action.
U.S. Appl. No. 10/909,117, Jan. 13, 2010, Notice of Allowance.
U.S. Appl. No. 10/909,117, Sep. 16, 2010, Notice of Allowance.
U.S. Appl. No. 10/909,117, Nov. 17, 2010, Issue Notification.
U.S. Appl. No. 10/909,118, Mar. 29, 2007, Office Action.
U.S. Appl. No. 10/909,118, Nov. 19, 2007, Office Action.
U.S. Appl. No. 10/909,118, May 12, 2008, Office Action.
U.S. Appl. No. 10/909,118, Jan. 5, 2009, Office Action.
U.S. Appl. No. 10/909,118, Jul. 24, 2009, Office Action.
U.S. Appl. No. 10/909,118, Jan. 13, 2010, Notice of Allowance.
U.S. Appl. No. 10/909,118, Sep. 21, 2010, Notice of Allowance.
U.S. Appl. No. 10/954,948, Mar. 15, 2007, Office Action.
U.S. Appl. No. 10/954,948, Nov. 16, 2007, Office Action.
U.S. Appl. No. 10/954,948, May 15, 2008, Office Action.
U.S. Appl. No. 10/954,948, Jan. 13, 2009, Office Action.
U.S. Appl. No. 10/954,948, May 29, 2009, Office Action.
U.S. Appl. No. 10/954,948, Jan. 13, 2010, Notice of Allowance.
U.S. Appl. No. 10/954,948, Jul. 6, 2010, Notice of Allowance.
U.S. Appl. No. 10/955,425, Mar. 15, 2007, Office Action.
U.S. Appl. No. 10/955,425, Nov. 16, 2007, Office Action.
U.S. Appl. No. 10/955,425, May 13, 2008, Office Action.
U.S. Appl. No. 10/955,425, Jan. 13, 2009, Office Action.
U.S. Appl. No. 10/955,425, May 28, 2009, Office Action.
U.S. Appl. No. 10/955,425, Feb. 26, 2010, Notice of Allowance.
U.S. Appl. No. 10/955,425, Jun. 25, 2010, Notice of Allowance.
U.S. Appl. No. 10/955,425, Sep. 30, 2010, Issue Notification.
U.S. Appl. No. 11/313,110, Jan. 8, 2008, Office Action.
U.S. Appl. No. 11/313,110, Jul. 2, 2008, Office Action.
U.S. Appl. No. 11/313,110, Mar. 3, 2009, Office Action.
U.S. Appl. No. 11/313,110, Nov. 2, 2009, Notice of Allowance.
U.S. Appl. No. 11/313,110, Feb. 18, 2010, Notice of Allowance.
U.S. Appl. No. 11/313,110, Jun. 15, 2010, Notice of Allowance.
U.S. Appl. No. 11/313,110, Sep. 29, 2010, Issue Notification.
U.S. Appl. No. 11/404,450, Feb. 4, 2009, Office Action.
U.S. Appl. No. 11/404,450, Mar. 17, 2009, Office Action.
U.S. Appl. No. 11/404,450, Sep. 30, 2009, Office Action.
U.S. Appl. No. 11/404,450, Apr. 22, 2010, Office Action.
U.S. Appl. No. 11/404,450, Nov. 26, 2010, Office Action.
U.S. Appl. No. 11/404,450, Aug. 10, 2011, Office Action.
U.S. Appl. No. 11/404,450, Jan. 31, 2012, Office Action.
U.S. Appl. No. 11/435,260, Jan. 10, 2008, Office Action.
U.S. Appl. No. 11/435,260, Mar. 26, 2008, Office Action.
U.S. Appl. No. 11/435,260, Dec. 16, 2008, Office Action.
U.S. Appl. No. 11/435,260, Jun. 18, 2009, Notice of Allowance.
U.S. Appl. No. 11/435,260, Jun. 26, 2009, Notice of Allowance.
U.S. Appl. No. 11/601,475, Jul. 22, 2008, Office Action.
U.S. Appl. No. 11/601,475, Jan. 6, 2009, Office Action.
U.S. Appl. No. 11/601,475, Jun. 1, 2009, Office Action.
U.S. Appl. No. 11/601,475, Jan. 15, 2010, Notice of Allowance.
U.S. Appl. No. 11/601,475, Jul. 9, 2010, Notice of Allowance.
U.S. Appl. No. 11/731,820, Jan. 27, 2010, Office Action.
U.S. Appl. No. 11/731,820, Aug. 5, 2010, Notice of Allowance.
U.S. Appl. No. 11/731,820, Dec. 16, 2010, Notice of Allowance.
U.S. Appl. No. 11/731,882, Feb. 3, 2010, Office Action.
U.S. Appl. No. 11/731,882, Sep. 1, 2010, Office Action.
U.S. Appl. No. 11/731,882, Aug. 29, 2011, Notice of Allowance.
U.S. Appl. No. 11/732,244, Sep. 28, 2009, Office Action.
U.S. Appl. No. 11/732,244, May 5, 2010, Notice of Allowance.
U.S. Appl. No. 11/732,244, Jun. 21, 2010, Notice of Allowance.
U.S. Appl. No. 11/732,244, Sep. 22, 2010, Issue Notification.
U.S. Appl. No. 11/805,584, Apr. 27, 2009, Office Action.
U.S. Appl. No. 11/805,584, Oct. 29, 2009, Office Action.
U.S. Appl. No. 11/805,584, Mar. 15, 2010, Office Action.
U.S. Appl. No. 11/805,584, Oct. 4, 2010, Office Action.
U.S. Appl. No. 11/805,584, May 12, 2011, Notice of Allowance.
U.S. Appl. No. 11/961,290, May 6, 2009, Office Action.
U.S. Appl. No. 11/961,290, Dec. 18, 2009, Office Action.
U.S. Appl. No. 11/961,384, May 26, 2009, Office Action.
U.S. Appl. No. 11/961,384, Oct. 8, 2009, Office Action.
U.S. Appl. No. 11/961,384, Apr. 23, 2012, Office Action.
U.S. Appl. No. 11/961,754, Jul. 22, 2009, Office Action.
U.S. Appl. No. 11/961,754, Apr. 5, 2010, Notice of Allowance.
U.S. Appl. No. 11/961,754, Jul. 28, 2010, Notice of Allowance.
U.S. Appl. No. 11/961,754, Nov. 23, 2010, Issue Notification.
U.S. Appl. No. 11/973,707, Jun. 9, 2009, Office Action.
U.S. Appl. No. 11/973,707, Mar. 19, 2010, Office Action.
U.S. Appl. No. 11/973,707, Oct. 12, 2011, Notice of Allowance.
U.S. Appl. No. 11/961,775, Oct. 1, 2009, Office Action.
U.S. Appl. No. 11/961,775, Mar. 31, 2010, Office Action.
U.S. Appl. No. 12/608,335, May 11, 2012, Office Action.
U.S. Appl. No. 12/875,971, Apr. 19, 2012, Office Action.
U.S. Appl. No. 12/895,032, Feb. 1, 2012, Office Action.
U.S. Appl. No. 12/895,032, Jul. 3, 2012, Office Action.
U.S. Appl. No. 12/949,481, Jan. 5, 2012, Office Action.
U.S. Appl. No. 12/949,481, Feb. 15, 2012, Office Action.
U.S. Appl. No. 12/966,916, Jun. 10, 2011, Office Action.
U.S. Appl. No. 12/966,916, Jan. 5, 2012, Office Action.
U.S. Appl. No. 12/966,916, May 23, 2012, Notice of Allowance.
Landers, Rüdiger and Mülhaupt, Rolf "Desktop manufacturing of complex objects, prototypes and biomedical scaffolds by means of computer-assisted design combined with computer-guided 3D plotting of polymers and reactive oligomers" Macromolecular Materials and Engineering , vol. 282, Issue 1, pp. 17-21, Oct. 2000.
U.S. Appl. No. 11/961,290, Aug. 3, 2012, Office Action.
U.S. Appl. No. 12/875,971, Jul. 26, 2012, Notice of Allowance.
U.S. Appl. No. 12/966,916, Aug. 1, 2012, Issue Notification.
U.S. Appl. No. 11/961,384, Aug. 21, 2012, Notice of Allowance.
U.S. Appl. No. 12/875,971, Oct. 17, 2012, Issue Notification.
U.S. Appl. No. 12/949,481, Aug. 13, 2012, Notice of Allowance.
U.S. Appl. No. 13/089,039, Oct. 16, 2012, Office Action.
U.S. Appl. No. 13/801,469, Mar. 13, 2013, Von Oepen et al.
U.S. Appl. No. 13/089,039, Jun. 28, 2013, Office Action.
U.S. Appl. No. 12/895,032, Aug. 13, 2013, Office Action.
U.S. Appl. No. 12/608,335, Dec. 2, 2013, Office Action.
U.S. Appl. No. 12/895,032, Oct. 29, 2013, Office Action.
U.S. Appl. No. 13/089,039, Sep. 26, 2013, Office Action.
U.S. Appl. No. 12/608,335, Mar. 3, 2014, Advisory Action.
U.S. Appl. No. 12/895,032, Mar. 14, 2014, Office Action.
U.S. Appl. No. 13/089,039, Apr. 14, 2014, Notice of Allowance.
U.S. Appl. No. 14/323,658, Jul. 3, 2014, Fierens et al.
U.S. Appl. No. 11/961,290, Aug. 19, 2014, Notice of Allowance.
U.S. Appl. No. 13/089,039, Aug. 6, 2014, Issue Notification.
U.S. Appl. No. 12/895,032, Jan. 30, 2015, OA.
U.S. Appl. No. 12/608,335, Apr. 9, 2015, Office Action.
U.S. Appl. No. 11/961,290, Dec. 12, 2012, Office Action.
U.S. Appl. No. 11/961,384, Dec. 5, 2012, Issue Notification.
U.S. Appl. No. 12/895,032, Aug. 13, 2015, Office Action.
U.S. Appl. No. 13/801,469, Jan. 12, 2016, Office Action.

* cited by examiner ly flexible stent be employed, for example,

FLEXIBLE STENT WITH TORQUE-ABSORBING CONNECTORS

CROSS-REFERENCE TO RELATED APPLICATIONS

The present application is a continuation application of U.S. patent application Ser. No. 11/973,707, filed on Oct. 9, 2007, which is a Continuation in Part application of U.S. patent application Ser. No. 11/805,584 filed on May 23, 2007, the entireties of which are incorporated herein by reference.

BACKGROUND OF THE INVENTION

1. The Field of the Invention

The present invention relates to a medical device. More particularly, the present invention relates to a flexible stent that provides elevated torque-absorbing properties.

2. The Relevant Technology

Atherosclerosis, sometimes called the hardening or clogging of the arteries, is an accumulation of cholesterol and fatty deposits, called plaque, on the inner walls of the arteries. Atherosclerosis causes a partial or total blockage of the arteries and, consequently, a reduced blood flow to the heart, legs, kidneys, or brain.

Traditionally, clogged arteries have been treated with surgical procedures that involve the removal of the diseased arterial tract. Angioplasty procedures, during which a stent is inserted in the diseased portion of the artery, have gained increased acceptance during the last two decades because of the reduced complexity of this procedure in comparison with other surgical procedures and because of the consequent reduction in risk and discomfort to the patient.

Referring first to FIG. 1, a stent 20 is a small tubular element that typically has a cylindrical structure 22 and that, once placed within a blocked vessel, acts as a scaffold that keeps the vessel open. Stent 20 may be implanted in a bodily vessel by disposing the stent over a balloon tipped catheter, by driving the stent to a target location in a vessel, and by subsequently inflating the balloon at the target location.

Alternatively, stent 20 may be caused to self-expand without the use of a balloon by manufacturing stent 20 from a shape memory material and by disposing stent 20 over a catheter in a contracted delivery configuration. Stent 20 is successively driven to a target location in a vessel, where a sheath covering stent 20 is withdrawn and stent 20 is allowed to self-expand. One type of self-expanding stent is produced from a superelastic material and is compressed inside the sheath into a contracted delivery configuration. When the stent is released from the sheath, the flexible material causes the stent to spring back to its original shape and size before compression. Another type of self-expanding stent is produced from a thermo-elastic shape-memory material that is formed into a desired size and shape and is then annealed at a temperature higher than a transition temperature. After cooling the stent to a temperature below the transition temperature, the stent becomes soft and can be reduced to a smaller size by crimping, so that it can be delivered to the target location, where the stent is warmed to a temperature above the transition temperature and returns to the preprogrammed size and shape. The present invention relates to both to balloon expandable stents and to self-expanding stents, as explained in greater detail in the following sections.

The stents in the prior art are formed as a metal mesh or, in general, as a web structure that provides some degree of flexibility. Certain types of anatomies require that stents with elevated degrees of flexibility be employed, for example, stents to be implanted in the carotid artery, because the bifurcated anatomy of the carotid artery and frequent movements of that part of the body require a stent that can adapt to such anatomy. The stent designs in the prior art typically increase flexibility by increasing cells size in the mesh or in the web structure. Therefore, whenever stent flexibility is increased in the stents in the prior art, scaffolding support is affected negatively due to the related reduction in web density.

A prior art stent is disclosed in U.S. Pat. No. 5,104,404, which teaches an articulated stent in which stent segments, formed by diamond-shaped cells disposed in ring form, are connected one to the other at some but not all of the tips of the diamond-shaped cells. This arrangement provides for a stent with a high degree of longitudinal flexibility, but also for limited support to the arterial walls at the junctions areas between the different stent segments.

With reference now to FIG. 2, other designs in the prior art have attempted to increase stent flexibility by forming the stent as a plurality of web rings 24 that are disposed longitudinally along tubular body 22 and that are coupled one to the other by flexible connectors 26. Designs of this type are disclosed in U.S. patent application Ser. No. 10/743,857, U.S. Pat. Nos. 6,682,554 and 6,602,285, International Application PCT/EP99/06456, and German Patent Application Serial No. 19840645.2, the entireties of which are incorporated herein by reference. The function of flexible connectors 26 is to facilitate the bending of stent 20 by creating longitudinal segments softer than web rings 24. At the same time, flexible connectors 26 transmit torque from one web ring 24 to adjacent web rings 24 when a bending force is applied to tubular body 22 or when a radial force is applied to tubular body 22, for example, during deployment of stent 22 from the contracted delivery configuration to the expanded delivery configuration. Such a transmission of torque may cause different web rings 24 to rotate differentially upon application of a bending force or upon deployment of stent 20.

One example of stent construction based on longitudinally alternating of web rings coupled by flexible connectors can be found in U.S. Pat. No. 6,190,403, which discloses a stent having a plurality of web rings disposed in longitudinal order. Each of the web rings is formed by longitudinally-oriented cells disposed circumferentially and is joined to a neighboring web ring by sinusoidal connectors that couple cell tips that are longitudinally aligned one with the other. The stent of the '403 patent provides an elevated degree of scaffolding to the arterial walls, though its structure provides only for a limited degree of longitudinal flexibility due to the limited extent of longitudinal translation that is possible between web rings when a compressive force is applied.

Another example of stent construction based on longitudinally alternating web rings coupled by flexible connectors can be found in U.S. Pat. No. 6,451,049, which discloses a stent having a plurality of waveform rings coupled by longitudinal connectors that include a "U" bend. This construction also provides for an elevated degree of scaffolding of the vessel walls, but its flexibility is constrained by the limited ability to compress of the flexible segments.

In order to increase stent flexibility, stent designs have been introduced in which the flexible connectors between web rings do not have a longitudinal orientation but instead have a transverse orientation. Examples of such stent designs can be found in U.S. Pat. Nos. 5,980,552; 6,059,811; 6,508,834; and 6,589,276. The transverse orientation of the flexible connectors induce the web rings to rotate one in relation to the other upon the application of a bending or radial force to the stent, and in order to reduce torsional stress in the stent during bending and during expansion, the flexible connectors may have alternating directions. For example, the flexible connectors connecting two neighboring rings may be oriented in a direction opposite to the direction of the next set of flexible connectors. If the web rings are prevented from rotating, the torsional stress in the stent becomes absorbed by the flexible connectors and by the web rings, possibly causing the connectors to warp along their entire length. Additionally, this type of construction causes a foreshortening of the stent during expansion.

This problem is illustrated in greater detail in FIGS. 3A-3B. A typical connector 28 couples first web ring 30 to second web ring 32 by connecting junction bend 34 on first ring 30 to junction bend 36 on second ring 32. In order for stent 38 to provide an elevated degree of scaffolding to the vessel within which stent 38 is implanted, each junction bend 34 on web ring 30 is coupled to a junction bend 36 in web ring 32, increasing stent density. The higher the density of stent 38, however, the lower the flexibility, which may be increased by increasing the length of connector 28.

When the length of connector 28 is increased, the bending capability and the flexibility of stent 38 is increased correspondingly because the moment applied by connector 28 to web rings 30 and 32 upon the application of a bending force on stent 34 is increased correspondingly. Unfortunately, long connectors disposed transversally on stent 38 can extend along a significant amount of the outer circumference of stent 38. For example, if stent 38 has a diameter of 1.6 mm and if connector 28 is one mm long, connector 28 extends for approximately 72 degrees along the circumference of stent 38. In turn, long connectors 28 will exert a significant amount of torque on junction bends 34 and 36, and, consequently, on web rings 30 and 32, and may warp along their entire length. In addition, long connectors 28 cause the size of stent cells to increase during expansion, therefore, long connectors cause a reduction in the scaffolding properties of stent 20, or a reduction in the ability of stent 20 to effectively support the vessel, into which stent 20 is implanted.

By having long connectors 28 disposed in a direction essentially perpendicular to the longitudinal axis of stent 20, connector 28 also tend to retain the bend radius of stent 20 during expansion and to cause a distortion of stent 20 in the expanded configuration.

Attempts have been made in the prior art to provide long connectors that extend along relatively limited portions of the circumference of stent 38 and that increase vessel support. For example, U.S. Pat. Nos. 5,449,373; 6,203,569; 6,740,114; 6,790,227; 6,942,689; 6,955,686; 6,998,060; 6,679,911; and 6,875,228 disclose stent constructions, in which the connectors have a variety of shapes in the form of the letters "M", "N", "W" or similar shapes, but which all include a plurality of segments oriented at certain angles with respect to the longitudinal axis of the stent. In particular, each of the prior art designs contains one or more central segments that are oriented at an angle with respect to the longitudinal axis of the stent, causing rotations in different degrees upon the application of a torsional force on the connector, for example due to a bending of the stent or during expansion.

Therefore, it would be desirable to provide a stent that generates an elevated degree of scaffolding to a bodily vessel while remaining highly flexible.

It would also be desirable to provide a stent, in which long connectors can be employed to increase stent flexibility and that can absorb torsional forces applied to the stent without warping along their entire lengths.

BRIEF SUMMARY OF THE INVENTION

A stent according to the present invention exhibits a highly flexible structure and elevated scaffolding properties, and at the same time is configured to absorb torque applied on the stent by bending or radial forces.

The stent according to the present invention is expandable from a contracted delivery configuration to an expanded deployed configuration and includes an essentially tubular body formed by a plurality of web rings disposed longitudinally. Each of the web rings is defined by a plurality of web elements that are disposed circumferentially and that, in the contracted delivery configuration, are substantially parallel to the longitudinal axis of the tubular body. Pairs of the web elements are sequentially adjoined at junction bends, and a junction bend in a first web ring is coupled to a junction bend in a neighboring web ring by one of the connectors.

Each of the connectors is formed by a plurality of segments disposed in a step-wise configuration. At least one of the connector segments is situated in a central position within the connector and is disposed with an orientation essentially parallel to the longitudinal axis of the stent. These connectors couple junction bends that are laterally offset one in relation to the other, making the connectors span diagonally along the profile of the tubular body.

The second segment may be rectilinear in shape and become twisted to acquire a helical curvature when a bending or expansion stress is applied to the stent. In one embodiment, the central element may be pre-deformed with a helical curvature in the contracted delivery configuration that becomes more accentuated during a bending or expansion of the stent. The central element may also be manufactured to have a cross-sectional area that is different from the cross-sectional areas of the end segments.

In one embodiment, each of the junction bends in the first web ring is connected to one junction bend in one neighboring web ring by one connector, so that each junction bend in one web ring is coupled to another junction bend in an adjacent web ring.

The stent of the present invention may be manufactured from a variety of materials, including metallic materials and plastic materials. When the stent is to be self-expanding, Nitinol or another shape memory material may be employed, while a balloon-expandable stent may be manufactured from stainless steel or other biocompatible metallic or plastic material. All or part of the stent (for example, the connector) may also be manufactured from a biodegradable material, for example, from a plastic absorbing material. In addition, the stent of the present invention may include a number of ancillary features known in the art, for example, may be coated with a bioactive agent or contain radio-opaque markers.

Methods of use of the stent according to the present invention are also provided.

BRIEF DESCRIPTION OF THE SEVERAL VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

The present invention relates to stent designs that can absorb an elevated degree of torque during expansion and after implantation in a patient while at the same time providing a highly flexible stent structure. One application of the present invention relates to closed cell stents, in particular, carotid stents, for which an elevated degree of lesion scaffolding and the capability of conforming to tortuous anatomies are key design features.

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
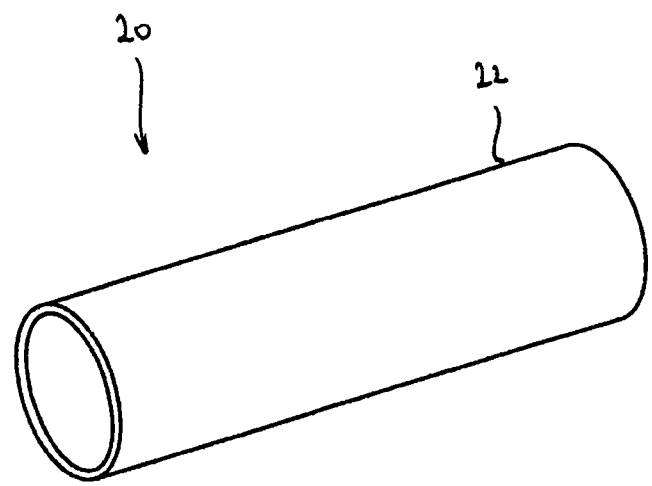
FIG. 1 is a perspective view of an essentially tubular body of a stent.
Figure 3A:
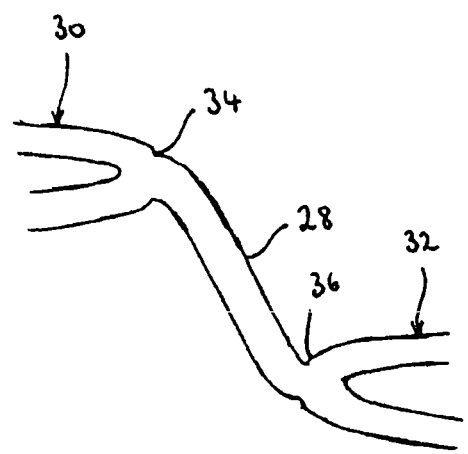
FIG. 3A illustrates a configuration of stent connector according to the prior art.
Figure 3B:
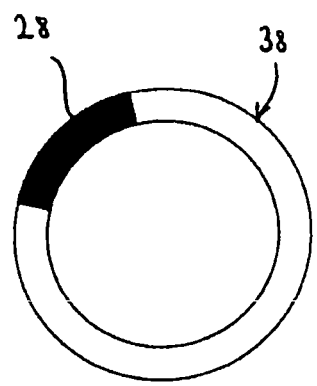
FIG. 3B is a schematic top view of the essentially tubular body of a stent highlighting the span of the connector of FIG. 3B when disposed within the tubular body.
Figure 2:
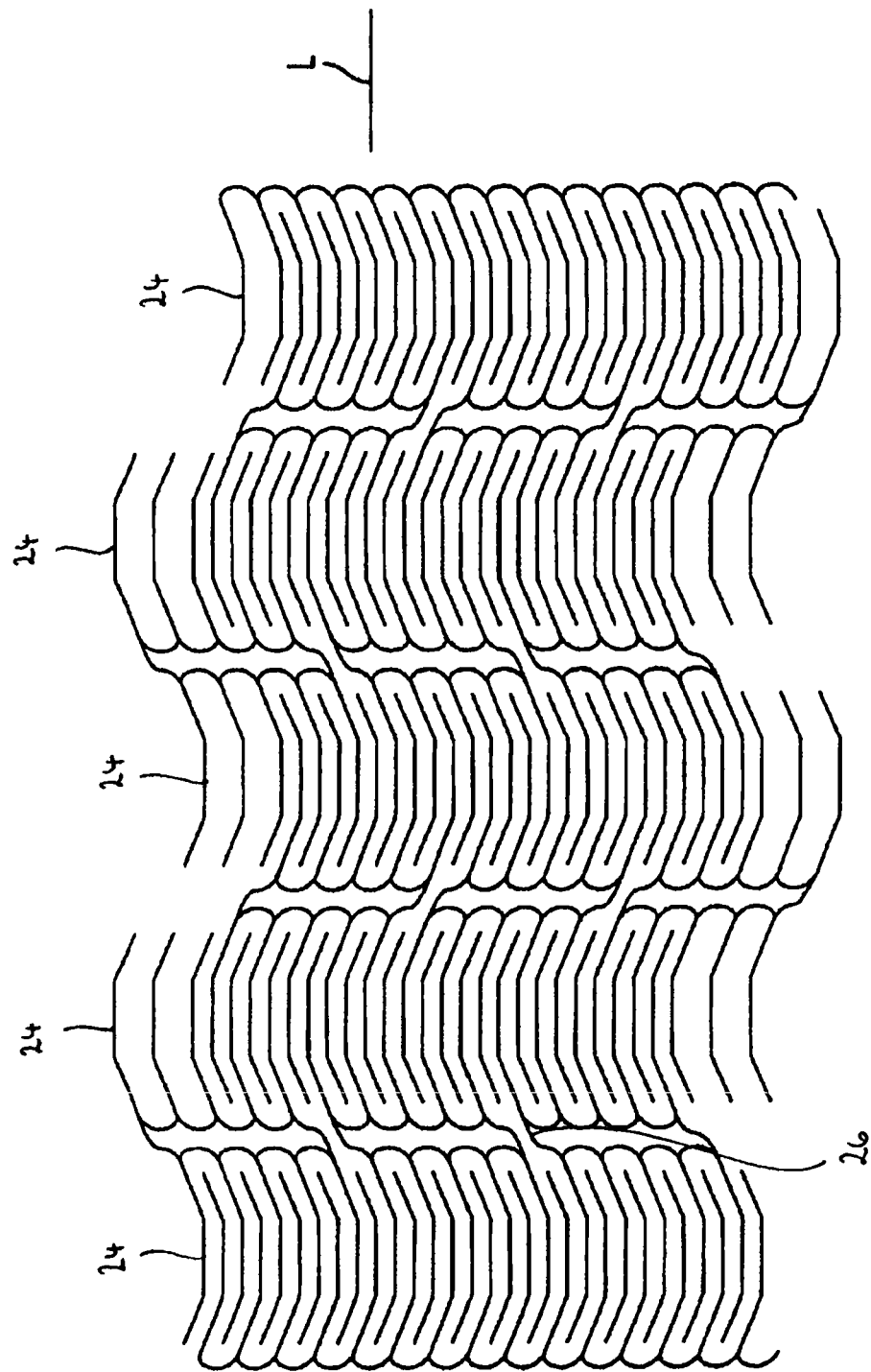
FIG. 2 is a front view of a stent connector according to the prior art.
Figure 4:
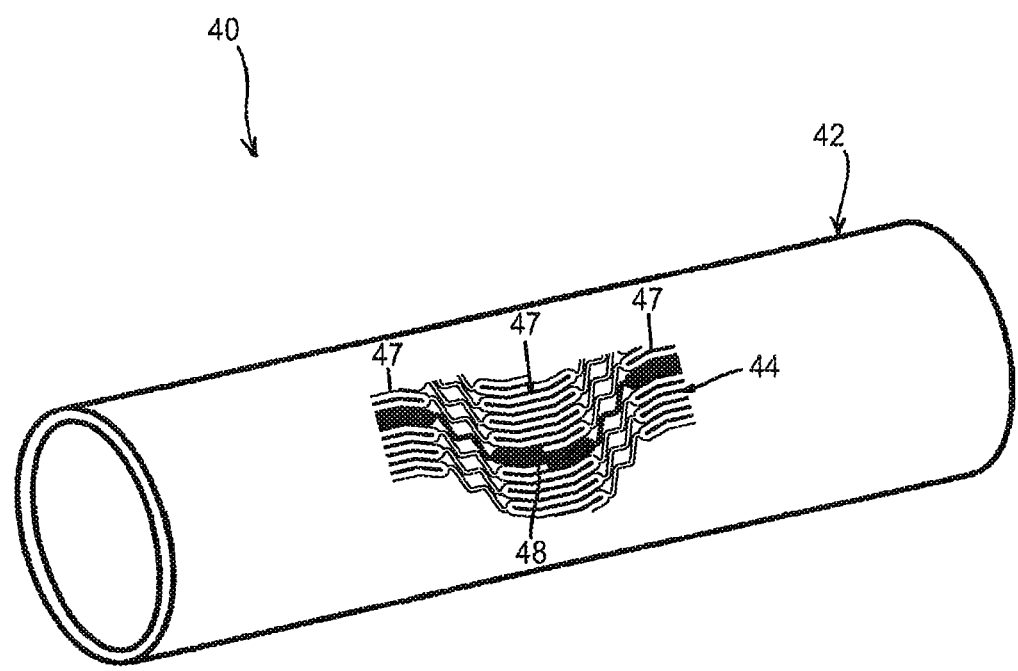
FIG. 4 is a perspective view of one embodiment of the present invention, showing the stent pattern in a detail view.

Referring to FIG. 4, a stent 40 constructed according to the principles of the present invention includes an essentially tubular body 42 expandable from a contracted delivery configuration to an expanded deployed configuration. While body 42 is depicted in FIG. 4 as essentially cylindrical in shape, body 42 may be provided with other shapes, for example, with a frustoconical shape or with the shape of a hyperboloid.

Body 42 is defined by a web structure 44, shown in FIG. 4 only in a detail view that relates to the contracted delivery configuration. Web structure 44 includes a plurality of web elements 46, each formed by a plurality of crowns 48.

Figure 5:
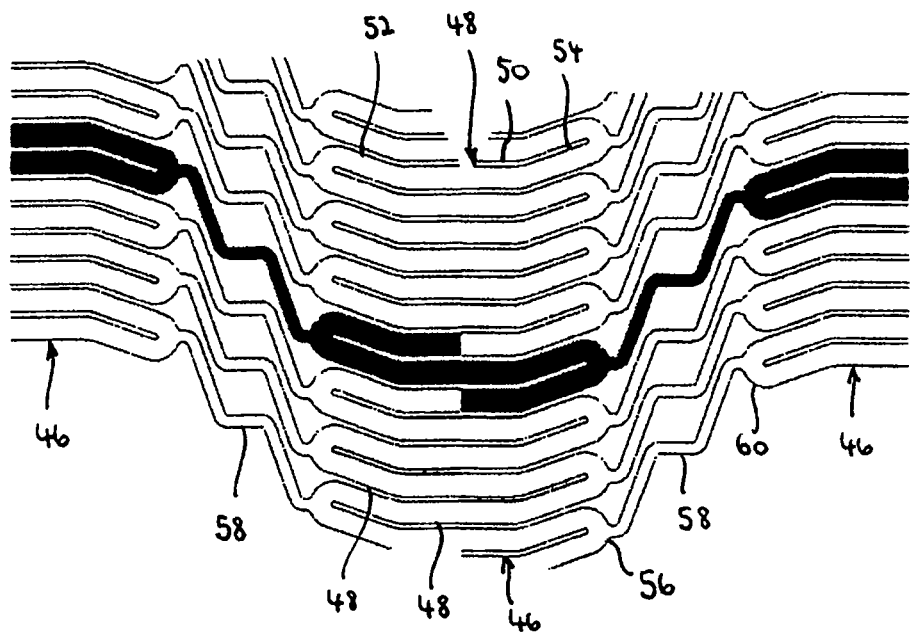
FIG. 5 is a detail view, illustrated as a flattened surface, of the web structure of a stent according to one embodiment of the present invention.

Referring now to FIG. 5, each crown 48 includes a central member 50 having a first end member 52 and a second end member 54 extending respectively from the opposite ends of central member 50. Central member 50, first end member 52 and second end member 54 are each essentially linear in shape, and, in the contracted delivery configuration of stent 40, central member 50 is disposed essentially parallel to the longitudinal axis of body 42 (see also FIG. 4), while first and second members 52 and 54 extend from central member 50 at obtuse angles. Preferably, first and second members 52 and 54 extend from central member 50 at the same angle, but in other embodiments, first and second members 52 and 54 may extend from central member 50 at different angles. In still other embodiments, one or more of central member 50 and first and second members 52 and 54 may be non-rectilinear and have a curved shape.

Crowns 48 are nested one into the other in the contracted delivery configuration and are sequentially adjoined at one end by a junction bend 56 that exhibits an essentially arcuate shape. A series of crowns 48 is disposed circumferentially about the longitudinal axis of body 42 to form web rings 46, which are joined one to the other by connectors 58. As shown in FIG. 5, the crowns in one web ring may be disposed with an orientation that is opposite to the orientation of the crowns in a neighboring web ring. In the illustrated embodiment, two adjacent web rings are disposed with an orientation of crowns 48 that is 180 degrees different one from the other.

Stent 40 may be manufactured from a variety of biocompatible materials, including metal and plastic materials. For example but not by way of limitation, stent 40 may be manufactured from Nitinol or other shape memory material if a self-expanding configuration of stent 40 is desired, or from stainless steel if balloon expansion is foreseen. Alternatively, stent 40 may be manufactured from a plastic material that enables either a permanent stent placement or a temporary stent placement, for example, from a plastic absorbing material.

In some embodiments, crowns 48 and connectors 58 may be manufactured from a biodegradable material when it is expected that only temporary vessel support is required. In another embodiment, only connectors 58 may be manufactured from a biodegradable material, so that the scaffolding provided by stent 40 may change over time and connectors 58 will gradually dissolve in the fluid carried by the vessel (for example, blood), leaving web rings 46 intact and allowing web rings 46 to be disposed at specific angles in relation to each other, as required by the patient's anatomy or by the movements of the patient's body.

Figure 5A:
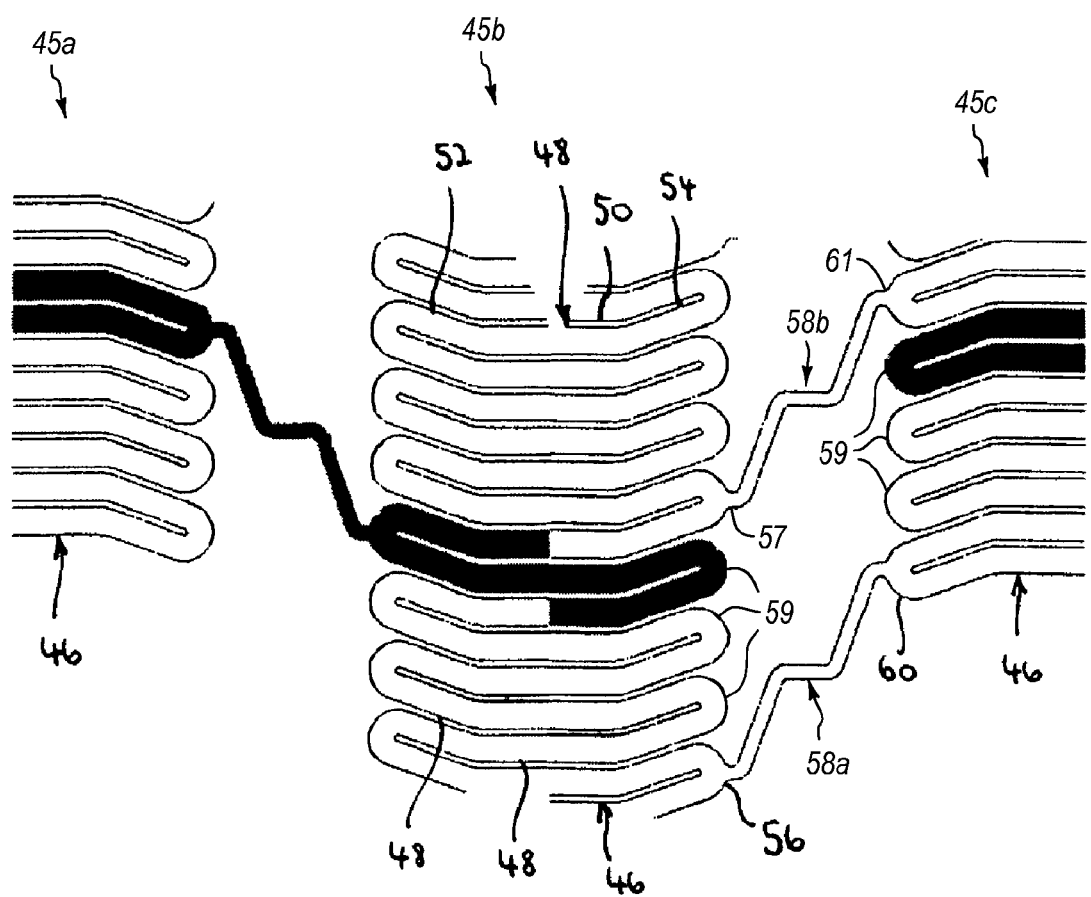
FIG. 5A is a detail view, illustrated as a flattened surface, of the web structure of a stent according to an embodiment of the present invention

While FIG. 5 illustrates that each junction bend 56 in one web ring is adjoined by connector 58 to a junction bend 60 in the adjacent web ring, only one out of a plurality of junction bends in one web ring (for example, one every three) may be adjoined to a junction bend in an adjacent web ring, providing stent 40 with larger open spaces between adjacent web rings 46. An example of which is shown in FIG. 5A. For example, the web ring 45a shown on the left is only connected to the web ring 45b in the middle by a single connector 58 (e.g. shown in black), such that the connector 58 is separated by at least seven junction bends 60. In another example, the web ring 45c on the right is connected to the web ring 45b in the middle by two connectors 58, such that the two connectors 58 are separated by three unadjoined junction bends 60. Thus, FIG. 5A illustrates an embodiment of an endoprosthesis configured to transition from a contracted delivery configuration to an expanded deployed configuration. The endoprosthesis includes a plurality of longitudinally adjacent web rings 45a-c defining an essentially tubular web structure, each web ring 45a-c including a plurality of adjoined web elements 46, 48. The endoprosthesis includes a plurality of junction bends 56, 60 adjoining pairs of the plurality of adjoined web elements 46, 48, a first junction bend 56 in a first web ring 45b of the plurality of longitudinally adjacent web rings 45a-c is connected to a second junction bend 60 in an adjacent neighboring web ring 46c of the plurality of longitudinally adjacent web rings 45a-c by a first S-shaped connector 58a, the second junction bend 60 being longitudinally offset from the first junction bend 56 and being circumferentially separated from the first junction bend 56, a third junction bend 57 in the first web ring 45b of the plurality of longitudinally adjacent web rings 45a-c is connected to a fourth junction bend 61 in the adjacent neighboring web ring 45c of the plurality of longitudinally adjacent web rings 45a-c by a second S-shaped connector 58b, the fourth junction bend 61 being longitudinally offset from the third junction bend 57 and being circumferentially separated from the third junction bend 57, the first junction bend 56 being circumferentially separated from the third junction bend 57 by at least three unadjoined junction bends 59, the first and second S-shaped connectors 58a, 58b having a plurality of segments disposed one in relation to the other in step-wise configuration, the plurality of segments being interconnected by connectors. While this more open design increases stent flexibility, the scaffolding properties of the stent are correspondingly decreased because of decreased stent density.

One aspect of the present invention is to provide an elevated degree of flexibility while retaining a closed cell structure, in which each junction bend 56 in one web ring 46 is coupled to a junction bend 60 in a neighboring web ring 46. Therefore, stent 40 is well suited for delivery and implantation at sites that require elevated flexibility and elevated scaffolding, for example, in carotid arteries. At the same time, the step-wise configuration of connectors 58 enables the use of connectors 58 which are relatively long, increasing flexibility to suit tortuous anatomies and various body movements, but through which the torsion of one web ring 46 in relation to the other is decreased or eliminated, as explained in greater detail below.

It should be observed that each of connectors 58 does not adjoin two junction bends that are longitudinally aligned, but instead adjoin two junction bends 56 and 60 that are laterally offset one in relation to the other. This offset configuration is more advantageous than a configuration linking adjacent junction bends. More specifically, a configuration with connectors 58 linking junction bends 56 and 60 that are offset one from the other provides an elevated degree of flexibility to stent 40, because in this configuration neighboring web rings have a greater ability to rotate one in relation to the other when stent 40 is deployed or becomes subjected to a bending stress.

Connectors 58 may join adjacent junction bends 56 and 60 at different points within the junction bends. For example, in the embodiment shown in FIG. 5 and, in greater detail, in FIG. 6, connector 58 adjoins essentially the middle points of junction bends 56 and 60 by extending from essentially the middle point of junction bend 56 to essentially the middle point of junction bend 60. In other embodiments, connector 58 may adjoin the lowest point in junction bend 56 with the highest point of junction bend 60, or the highest point of junction bend 56 with the lowest point of junction bend 60. It should be understood that in still other embodiments, connectors 58 may join junction bends 56 and 60 at a plurality of different points of the junction bends, and that some of the crowns 46 and connectors 58 are shown in FIGS. 5 and 6 in darkened color only for illustrative purposes and not for indicating any particular structural or design differences from the neighboring crowns and connectors.

Figure 6:
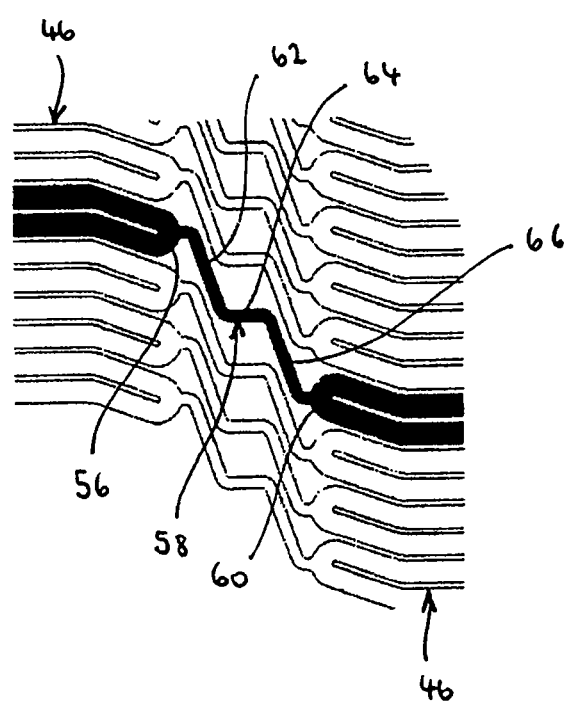
FIG. 6 is a detail view of the web structure of FIG. 5.
Figure 7:
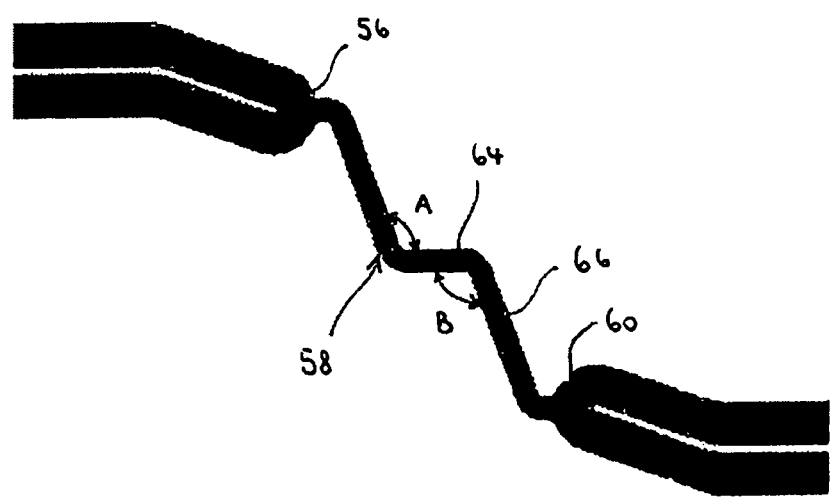
FIG. 7 is a schematic plan view of a connector connecting two neighboring junction bends according to one embodiment of the present invention.

The structure and mode of operation of connector 58 is illustrated in greater detail in FIGS. 6 and 7. More particularly, connector 58 includes a first segment 62, a second (middle) segment 64 and a third segment 66, disposed one in relation to the other in a step-wise configuration. Within the structure of connector 58, first segment 62 couples connector 58 with junction bend 56, third connector 66 couples connector 58 with junction bend 60, while second segment 64 couples first segment 62 with third segment 66. Second segment 64 is arranged in a direction essentially parallel to the longitudinal axis of body 42, while first segment 62 and third segment 66 are arranged at an angle A with respect to second segment 64, for example, 110 degrees as shown in FIG. 7. In different embodiments, connector 58 may be composed of different numbers of segments, which may further be arranged at angles of varying amplitudes, for example, between 100 and 170 degrees.

Figure 8:
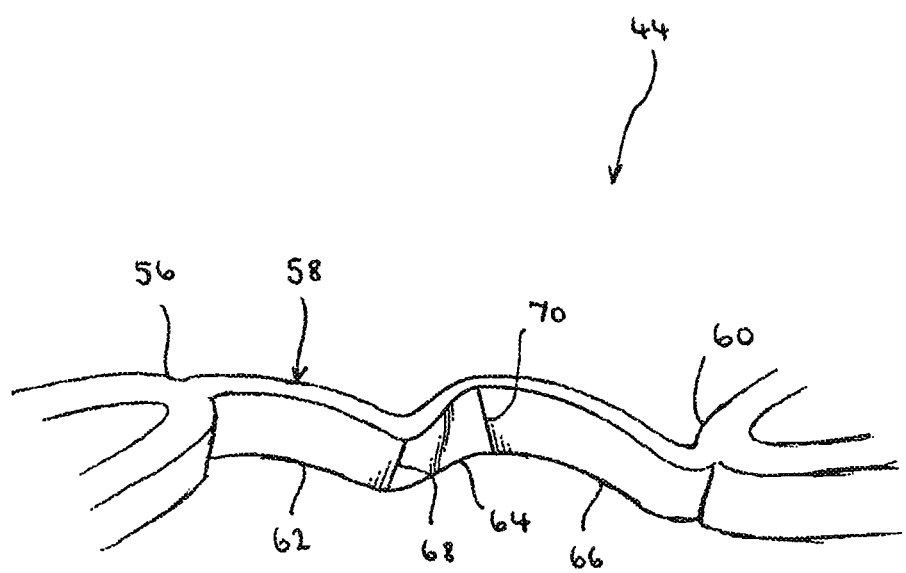
FIG. 8 is a perspective view of the connector of FIG. 7.

Referring now to FIGS. 7 and 8, the configuration of connector 58 is such to absorb a torsional stress applied to body 42, particularly during expansion of the stent from the contracted delivery configuration to the expanded deployed configuration. Such an ability to absorb torque is provided not only by the relative movements of first segment 62 and third segment 66, by which the widths of angle A between second segment 64 and first segment 62, and of angle B between second segment 64 and third segment 66, may change as a consequence of torsional stress, but also by the twisting motion of second segment 64 to assume an essentially helical shape. By the twisting motion of second segment 64, the torsional stress from, for example, first segment 62 is not entirely transmitted to third segment 66, but is absorbed (entirely or partially) by the twisting motion of second segment 64.

By disposing second segment 64 in a direction essentially parallel to the longitudinal axis of tubular body 42, torque developing, for example, during deployment of the stent is absorbed at a much greater rate than in stent configurations having second segment 64 disposed at an angle in relation to the longitudinal axis of tubular body 42. Therefore, the connector design of the present invention absorbs torque at a greater rate than, for example, designs where the connectors between the web rings have shapes reminiscent of the letters "N" or "W", because the structure of connector 58 according to the present invention minimizes or eliminates the relative rotations of one web ring 46 in relation of a neighboring web ring 46. At the same time, second segment 64 provides for a greater scaffolding of the vessel walls than connector designs in which no step-like pattern is present, in particular, than designs having no longitudinally disposed segments. By having second segment 64 disposed essentially parallel to the longitudinal axis of tubular body 42, second segment 64 can become twisted, minimizing or eliminating the distortion problems in stents of the prior art that have long connectors, and improving surface contact of stent 40 with the vessel, within which stent 40 is disposed.

FIG. 8 illustrates in greater detail that second segment 64 has become deflected after the application of torsional stress on web structure 44, for example, when web structure 44 is expanded during the deployment of stent 40 and the web rings on which junction bends 56 and 60 are situated tend to rotate one with respect to the other. During such absorption of torque, connecting area 68 between first segment 62 and second segment 64 may become tilted in a direction opposite to that of connecting area 70 between second segment 64 and third segment 66 when second segment 64 assumes a helical disposition. This phenomenon is particularly relevant when stent 40 is manufactured by producing its shape from a tube, for example through a laser cutting process, so that connectors 58 exhibit edges that are substantially square. In one embodiment of the invention, the twisting motion of second segment 64 towards a helical disposition may be facilitated by manufacturing connector 58 with connecting areas 68 and 70 disposed not one parallel to each other, but instead at an angle one with respect to the other.

Stent 40 may be disposed into a target vessel location, for example, in a location within a carotid artery, by inserting a guide wire into the artery, and by successively translating a catheter along the guide wire that carries the stent in a contracted condition. When the stent has reached the target location, as may be determined by tracking radio-opaque markers embedded in the stent, a balloon disposed on the catheter and within the stent is inflated, causing the stent to expand from the contracted condition to the deployed condition until contact with the vessel walls is achieved. Alternatively, if the stent is manufactured from a self-expanding material, after the target location has been reached, a sheath covering the stent is withdrawn, enabling the stent to self-expand until contact with the vessel walls is made and a support structure is created.

By providing a stent having a structure formed by web elements that are disposed in web rings and that are coupled by connectors in the manner described herein, so to form a closed cell structure, an improved support is provided to the vessel walls in comparison with open cell stents, and a highly flexible structure is achieved that provides an elevated degree of scaffolding support to the vessel walls even when the vessel is bent.

Stent 40 may include different features known in the art to provide certain beneficial properties. For example but not by way of limitation, stent 40 may be coated with a therapeutic coating that includes a bioactive agent, or may contain radiopaque markers, or may be coupled to a fabric that prevents the passage of emboli from the vessel wall into the blood stream.

It should be noted that, while the invention has been described in connection with the above described embodiments, it is not intended to limit the scope of the invention to the particular forms set forth, but on the contrary, it is intended to cover such alternatives, modifications, and equivalents as may be included within the scope of the invention. Accordingly, the scope of the present invention fully encompasses other embodiments that may become obvious to those skilled in the art and the scope of the present invention is limited only by the appended claims.

What is claimed is:

1. An endoprosthesis configured to transition from a contracted delivery configuration to an expanded deployed configuration, the endoprosthesis comprising:
    a plurality of longitudinally adjacent web rings defining an essentially tubular web structure, each web ring including a plurality of adjoined web elements; and
    a plurality of junction bends adjoining pairs of the plurality of adjoined web elements, a first junction bend in a first web ring of the plurality of longitudinally adjacent web rings is connected to a second junction bend in an adjacent neighboring web ring of the plurality of longitudinally adjacent web rings by a first S-shaped connector, the second junction bend being longitudinally offset from the first junction bend and being circumferentially separated from the first junction bend by a plurality of unadjoined junction bends, a third junction bend in the first web ring of the plurality of longitudinally adjacent web rings is connected to a fourth junction bend in the adjacent neighboring web ring of the plurality of longitudinally adjacent web rings by a second S-shaped connector, the fourth junction bend being longitudinally offset from the third junction bend and being circumferentially separated from the third junction bend, the first junction bend being circumferentially separated from the third junction bend by at least three unadjoined junction bends, the first and second S-shaped connectors having a plurality of segments disposed one in relation to the other in step-wise configuration, the plurality of segments being interconnected by connectors.

2. The endoprosthesis of claim 1, wherein a central segment of the plurality of segments within the connector is disposed in a direction essentially parallel to a longitudinal axis of the essentially tubular web structure.

3. The endoprosthesis of claim 1, wherein the S-shaped connector is disposed within a gap disposed between the adjacent web rings.

4. The endoprosthesis of claim 1, wherein each of the web elements comprises a central member having a first and a second ends, wherein the central member is disposed essentially parallel to a longitudinal axis in the contracted delivery configuration, wherein the central member is connected at the first end to a first end member at a first obtuse angle, and wherein the central member is connected at the second end to a second end member at a second obtuse angle.

5. The endoprosthesis of claim 4, wherein the first and the second obtuse angles are essentially equal.

6. The endoprosthesis of claim 4, wherein the web elements of each web ring are nested one into the other in the contracted delivery configuration, and wherein the junction bends have an arcuate shape.

7. The endoprosthesis of claim 4, wherein the web elements in the first web ring are oriented at approximately 180 degrees in relation to the web elements in the neighboring web ring.

8. The endoprosthesis of claim 1, wherein the S-shaped connectors have a cross-sectional area different from the cross-sectional area of the web elements.

9. An endoprosthesis configured to transition from a contracted delivery configuration to an expanded deployed configuration, the endoprosthesis comprising:
    a plurality of longitudinally adjacent web rings defining a web structure, each web ring including a plurality of sequentially adjoined web elements,
    a plurality of junction bends in each of the plurality of longitudinally adjacent web rings, pairs of the plurality of sequentially adjoined web elements being sequentially adjoined at individual junction bends of the plurality of junction bends; and
    a plurality of S-shaped connectors joining adjacent web rings of the plurality of longitudinally adjacent web rings in a step-wise configuration, each S-shaped connector of the plurality of S-shaped connectors extending between a first junction bend in a first web ring of the plurality of longitudinally adjacent web rings and a second junction bend in a second web ring of the plurality of longitudinally adjacent web rings, the second junction bend being longitudinally offset and circumferentially separated from the first junction bend by at least two unadjoined junction bends, a third junction bend in the first web ring of the plurality of longitudinally adjacent web rings is connected to a fourth junction bend in the adjacent neighboring web ring of the plurality of longitudinally adjacent web rings by a second S-shaped connector, the fourth junction bend being longitudinally offset from the third junction bend and being circumferentially separated from the third junction bend, the first junction bend being circumferentially separated from the third junction bend by at least three unadjoined junction bends to form an open connected structure between the adjacent web rings, the first and second S-shaped connectors having a plurality of segments interconnected by connectors, the endoprosthesis being formed of a superelastic material,
    wherein the S-shaped connector is configured to twist as the endoprosthesis transitions from a contracted delivery configuration to an expanded deployed configuration.

10. The endoprosthesis of claim 9, wherein the second junction bend is circumferentially offset in a clockwise direction from the first junction bend about the web structure and another second junction bend is circumferentially offset in a counter-clockwise direction from another first junction bend.

11. The endoprosthesis of claim 9, wherein a central segment of the S-shaped connector is disposed in a direction essentially parallel to a longitudinal axis of the web structure.

12. The endoprosthesis of claim 9, wherein the S-shaped connector comprises a first segment, a second segment, and a central segment disposed between the first segment and the second segment, a junction between the first segment and the central segment being non-parallel to a junction between the second segment and the central segment.

13. The endoprosthesis of claim 12, wherein the junction between the first segment and the central segment and the junction between the second segment and the central segment are transverse to a longitudinal axis of the web structure.

14. The endoprosthesis of claim 12, the junction between the first segment and the central segment is tilted in a direction opposite the junction between the second segment and the central segment when in a deployed configuration.

15. The endoprosthesis of claim 12, wherein an angle between the first segment and the central segment, and the central segment and the second segment, is between about 45 and 135 degrees or about 100 and 170 degrees.

16. A method of deploying an endoprosthesis in a body lumen, the method comprising:
  locating an endoprosthesis in a contracted delivery configuration in the body lumen, the endoprosthesis comprising:
    a plurality of longitudinally adjacent web rings defining an essentially tubular web structure, each web ring including a plurality of adjoined web elements; and
    a plurality of junction bends adjoining pairs of the plurality of adjoined web elements, a junction bend in a first web ring of the plurality of longitudinally adjacent web rings is connected to a second junction bend in an adjacent neighboring web ring of the plurality of longitudinally adjacent web rings by an S-shaped connector, the second junction bend being longitudinally offset from the first junction bend and being circumferentially separated from the first junction bend by a plurality of unadjoined junction bends, a third junction bend in the first web ring of the plurality of longitudinally adjacent web rings is connected to a fourth junction bend in the adjacent neighboring web ring of the plurality of longitudinally adjacent web rings by a second S-shaped connector, the fourth junction bend being longitudinally offset from the third junction bend and being circumferentially separated from the third junction bend, the first junction bend being circumferentially offset from the third junction bend by at least three unadjoined junction bends, the first and second S-shaped connectors having a plurality of segments disposed one in relation to the other in step-wise configuration, the plurality of segments being interconnected by connectors,
  disposing the endoprosthesis in a location of the body lumen to receive the endoprosthesis in an expanded deployed configuration; and
  deploying the endoprosthesis to transition the endoprosthesis from the contracted delivery configuration to the expanded deployed configuration.

17. The method of claim 16, wherein the S-shaped connector comprises three segments, two segments of the three segments being essentially parallel, wherein deploying the endoprosthesis comprises translating one of the two essentially parallel segments relative to the other essentially parallel segments by application of a bending force on the essentially tubular web structure.

18. The method of claim 16, wherein deploying the endoprosthesis further comprises applying pressure to an interior surface of the essentially tubular web structure.

19. The method of claim 16, wherein disposing the endoprosthesis comprises advancing the endoprosthesis through the body lumen.

20. The endoprosthesis of claim 1, wherein the second junction bend is circumferentially separated from the first junction bend by at least two unadjoined junction bends.

21. An endoprosthesis configured to transition from a contracted delivery configuration to an expanded deployed configuration, the endoprosthesis comprising:
  a plurality of longitudinally adjacent web rings defining a web structure, each web ring including a plurality of sequentially adjoined web elements,
  a plurality of junction bends in each of the plurality of longitudinally adjacent web rings, pairs of the plurality of sequentially adjoined web elements being sequentially adjoined at individual junction bends of the plurality of junction bends; and
  a plurality of S-shaped connectors joining adjacent web rings of the plurality of longitudinally adjacent web rings in a step-wise configuration, each S-shaped connector of the plurality of S-shaped connectors extending between a first junction bend in a first web ring of the plurality of longitudinally adjacent web rings and a second junction bend in a second web ring of the plurality of longitudinally adjacent web rings, the second junction bend being longitudinally offset and circumferentially separated from the first junction bend by at least two unadjoined junction bends, a third junction bend in the first web ring of the plurality of longitudinally adjacent web rings is connected to a fourth junction bend in the adjacent neighboring web ring of the plurality of longitudinally adjacent web rings by a second S-shaped connector, the fourth junction bend being longitudinally offset from the third junction bend and being circumferentially separated from the third junction bend, the first junction bend being circumferentially separated from the third junction bend by at least three unadjoined junction bends to form an open connected structure between the adjacent web rings, the first and second S-shaped connectors having a plurality of segments interconnected by connectors, the endoprosthesis being formed of a superelastic material,
  wherein the S-shaped connector is configured to absorb torsional stress as the endoprosthesis transitions from a contracted delivery configuration to an expanded deployed configuration, the S-shaped connector comprising a first segment, a second segment, and a third segment disposed one in relation to the other in a step-wise configuration which allows relative movements of the first segment and the third segment and a twisting motion of the second segment such that the torsional stress from the first segment is not entirely transferred to the third segment.

* * * * *